(12) United States Patent
Stone

(10) Patent No.: US 7,736,364 B2
(45) Date of Patent: Jun. 15, 2010

(54) METHOD AND APPARATUS FOR PERFORMING ACL RECONSTRUCTION

(75) Inventor: Kevin T Stone, Winona Lake, IN (US)

(73) Assignee: Biomet Sports Medicine, LLC, Warsaw, IN (US)

(*) Notice: Subject to any disclaimer, the term of this patent is extended or adjusted under 35 U.S.C. 154(b) by 357 days.

(21) Appl. No.: 11/346,534

(22) Filed: Feb. 2, 2006

(65) Prior Publication Data

US 2007/0191853 A1 Aug. 16, 2007

(51) Int. Cl.
*A61B 17/00* (2006.01)
*A61F 2/08* (2006.01)

(52) U.S. Cl. ..................... 606/80; 623/13.12
(58) Field of Classification Search ............ 606/79, 606/86, 80, 86 R–88, 96; 623/13.11–13.2
See application file for complete search history.

(56) References Cited

U.S. PATENT DOCUMENTS

| | | | |
|---|---|---|---|
| 4,381,770 A | 5/1983 | Neufeld | |
| 4,383,527 A | 5/1983 | Asnis et al. | |
| 4,739,751 A | 4/1988 | Sapega et al. | |
| 4,744,353 A | 5/1988 | McFarland | |
| 4,787,377 A | 11/1988 | Laboureau | |
| 4,920,958 A | 5/1990 | Walt et al. | |
| 4,945,904 A | 8/1990 | Bolton et al. | |
| 5,139,520 A | 8/1992 | Rosenberg | |
| D331,464 S | 12/1992 | Rosenberg et al. | |
| 5,190,548 A | 3/1993 | Davis | |
| 5,257,996 A | 11/1993 | McGuire | |
| 5,314,429 A | 5/1994 | Goble | |
| 5,320,115 A | 6/1994 | Kenna | |
| 5,320,626 A | 6/1994 | Schmieding | |
| 5,324,295 A | 6/1994 | Shapiro | |
| 5,374,269 A | 12/1994 | Rosenberg | |
| 5,385,567 A | 1/1995 | Goble | |
| D357,534 S | 4/1995 | Hayes | |
| D359,557 S | 6/1995 | Hayes | |
| 5,514,144 A | 5/1996 | Bolton | |
| 5,520,693 A | 5/1996 | McGuire et al. | |
| 5,584,839 A | 12/1996 | Gieringer | |

(Continued)

OTHER PUBLICATIONS

Ozkan, Illhan, A Comparison between Tendon-bone Contact areas of Autografts Prepared for Single or Double Tunnel Anterior Cruciate Ligament Reconstructions, 2005, Joint Dis Rel Surg, 16(1): 16-19.*

(Continued)

*Primary Examiner*—Eduardo C Robert
*Assistant Examiner*—Ellen C Hammond
(74) *Attorney, Agent, or Firm*—Harness, Dickey

(57) ABSTRACT

A method and apparatus for drilling a bone for receipt of a first and second bundle includes drilling a first tunnel in the bone. A locating member extending along a first axis from the tool may be positioned into the first tunnel. A cutting guide may be moved relative to the locating member to define a lateral offset between the locating member and the cutting guide. The cutting guide may then be located at a desired offset. The second tunnel may then be formed in the bone with a cutting member associated with the cutting guide, the cutting member having a second axis in a defined orientation relative to the first axis.

17 Claims, 8 Drawing Sheets

U.S. PATENT DOCUMENTS

| | | | |
|---|---|---|---|
| 5,603,716 | A | 2/1997 | Morgan et al. |
| D378,780 | S | 4/1997 | Shuler |
| 5,624,295 | A | 4/1997 | Watkins |
| 5,643,273 | A | 7/1997 | Clark |
| 5,785,714 | A | 7/1998 | Morgan et al. |
| D398,996 | S | 9/1998 | Simmons et al. |
| 5,891,150 | A | 4/1999 | Chan |
| 5,968,050 | A | 10/1999 | Torrie |
| D420,132 | S | 2/2000 | Bucholz et al. |
| 6,019,767 | A | 2/2000 | Howell |
| 6,086,592 | A | 7/2000 | Rosenberg et al. |
| D433,506 | S | 11/2000 | Asfora |
| 6,187,011 | B1 | 2/2001 | Torrie |
| 6,210,415 | B1 | 4/2001 | Bester |
| 6,254,604 | B1 | 7/2001 | Howell |
| 6,254,605 | B1 | 7/2001 | Howell |
| 6,325,804 | B1 * | 12/2001 | Wenstrom et al. ........ 623/13.12 |
| 6,352,538 | B2 | 3/2002 | McGuire et al. |
| 6,623,524 | B2 * | 9/2003 | Schmieding ............. 623/13.14 |
| 6,712,849 | B2 * | 3/2004 | Re et al. .................. 623/13.14 |
| 6,716,217 | B2 * | 4/2004 | McKernan et al. ............ 606/98 |
| 6,878,150 | B1 | 4/2005 | McGuire et al. |
| 7,077,863 | B2 * | 7/2006 | Schmieding et al. ..... 623/13.14 |
| 7,270,666 | B2 * | 9/2007 | Lombardo et al. .......... 606/308 |
| 7,326,247 | B2 * | 2/2008 | Schmieding et al. ..... 623/13.14 |
| 2003/0009173 | A1 | 1/2003 | McGuire et al. |
| 2003/0216742 | A1 | 11/2003 | Wetzler et al. |
| 2005/0228399 | A1 * | 10/2005 | Kubo et al. ................... 606/96 |
| 2006/0271059 | A1 * | 11/2006 | Reay-Young et al. ......... 606/96 |
| 2007/0191853 | A1 | 8/2007 | Stone |
| 2008/0275453 | A1 * | 11/2008 | Lafosse et al. ................ 606/96 |
| 2009/0149858 | A1 * | 6/2009 | Fanelli et al. ................. 606/80 |

OTHER PUBLICATIONS

Bellier, G., Christel, P., Djian, P., Two-Bundle ACL Reconstruction Using Hamstring Tendons, 2005; Paris, France Power Point Presentation.*

"AANA Specialty Day 2003 Update on PCL Surgery Techniques," by Don Johnson MD found at http://www.carletonsportsmed.com/2003%20Update%20on%20PCL%20Surgery%20Techniques.pdf., 8 sheets.

"ACL Reconstruction: One Tunnel Without PCL Impingement is Similar to Two-Tunnel ACL Reconstruction" by Stephen M. Howell, MD, copyright 2004 Arthrotek, Inc. 26 sheets.

"Anatomic ACL Double-Bundle Reconstruction," by Ferretti, et al. printed article online dated Sep. 12, 2005.

"EZ Loc Femoral Fixation Device," copyright 2005 Arthrotek, Inc. 8 sheets.

"Fanelli PCL/ACL Guide, Rationale and Surgical Technique" by Gregory C. Fanelli, MD, copyright 2002 Arthrotek, Inc. 8 sheets.

"Howell™ 65° Tibial Guide," copyright 2002, Arthrotek, Inc. 8 sheets.

"Two-Bundle Posterior Cruciate Ligament Reconstruction—An In Vitro Analysis of Graft Placement and Tension," Mannor, et al. pp. 833-845, copyright 2000 American Orthopaedic Society for Sports Medicine—The American Journal of Sports Medicine, vol. 28, No. 6.

* cited by examiner

METHOD AND APPARATUS FOR PERFORMING ACL RECONSTRUCTION

FIELD

This invention relates generally to a method and apparatus for use in performing ACL reconstruction, and more particularly, to a method and apparatus for locating an anterior medial bundle and a posterior bundle in a two bundle ACL reconstruction.

BACKGROUND

Many people today are involved in a sport or some other type of physical activity. Some of these activities involve a low risk chance of injury, such as walking and swimming, while others involve a high risk chance or injury, such as football and skiing.

Damaged ligaments, cartilage and tendons in joints are not an uncommon occurrence, particularly in some of these high risk activities and sports. One of the joints which requires particular skill and presents particular difficulties in repairing is the knee joint.

Numerous improvements in repairing damage to knee joints have been made over the years, and some of the major advances involve the use of endoscopic techniques and arthroscopic procedures. Arthroscopic surgery is particularly useful in excising or repairing damaged knee cartilage.

Endoscopic techniques have also been developed for use in repair and reconstruction of damaged anterior cruciate ligaments (ACL) and posterior cruciate ligaments (PCL). When the ACL in particular has ruptured and is non-repairable, it is usually replaced in young adults and the knee reconstructed through use of grafts (biological or synthetic).

In one surgical technique a single bundle reconstruction is performed to replace a torn ACL. In such a technique, a single tibial tunnel is prepared in the tibia and a single complementary femoral tunnel is prepared in the femur. In one example, U.S. Pat. No. 6,254,605 to Howell discloses methods and instruments for preparing the tibial and femoral tunnels.

In another surgical technique a dual bundle reconstruction is performed to replace a torn ACL. In a dual bundle technique, a first bundle is implanted anteromedially on the tibial site. This bundle is referred to as an anterior medial (AM) bundle. A second bundle is implanted posterolaterally on the tibial site. This bundle is referred to as a posterior lateral (PL) bundle.

To accommodate both bundles, an AM tunnel and a PL tunnel are prepared in the femur. Correct placement of the AM and PL tunnels is vital to a successful dual bundle ACL reconstruction. Incorrect tunnel placement may be a cause of failure in an ACL reconstruction. In some cases of dual bundle reconstruction however, it is difficult to accurately position one tunnel relative to the other tunnel.

SUMMARY

A method for drilling a bone for receipt of a first and second bundle includes drilling a first tunnel in the bone. A locating member extending along a first axis from the tool may be positioned into the first tunnel. A cutting guide may be moved relative to the locating member to define a lateral offset between the locating member and the cutting guide. The cutting guide may then be located at a desired offset. The second tunnel may then be formed in the bone with a cutting member associated with the cutting guide, the cutting member having a second axis in a defined orientation relative to the first axis.

In one example, moving the cutting guide includes translating the cutting guide in a direction along its axis. A first perpendicular distance may be defined from a point on the cutting member to the locating member, wherein translation of the cutting guide along its axis defines a second perpendicular distance from the point on the cutting member to the locating member and wherein the first and second distances are distinct. In another example, moving the cutting guide includes moving the cutting guide in a direction lateral to its axis.

A tool for preparing a second tunnel relative to a first tunnel in bone includes a first longitudinal member having a locating member extending therefrom. The locating member may be adapted to be inserted into the first tunnel. A second longitudinal member includes a cutting member extending from a distal end. The second longitudinal member may be moveable relative to the first longitudinal member to define a desired offset between the cutting member and the locating member.

Further areas of applicability of the present disclosure will become apparent from the detailed description provided hereinafter. It should be understood that the detailed description and various examples, while indicating various embodiments of the invention, are intended for purposes of illustration only and are not intended to limit the scope of the following claims.

BRIEF DESCRIPTION OF THE FIGURES

The present invention will become more fully understood from the detailed description and the accompanying drawings, wherein.

DETAILED DESCRIPTION OF VARIOUS EMBODIMENTS

Figure 1:
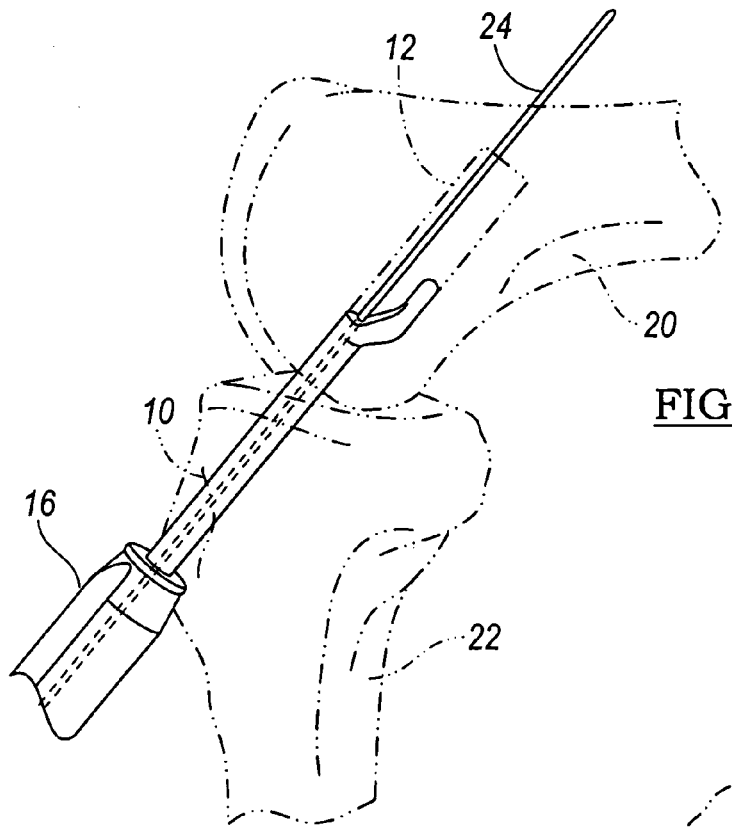
FIG. 1 is a lateral view of a tibia and femur in phantom shown with an exemplary femoral aimer inserted through a tibial tunnel and a graft passing pin drilled through the lateral thigh according to an exemplary method.

The following description of various embodiment(s) is merely exemplary in nature and is in no way intended to limit the application or uses. Those skilled in the art will appreciate that the following teachings can be used in a much wider variety of applications than the examples specifically mentioned herein. More specifically, while the following discussion is specifically directed toward a tool and method for dual bundle ACL reconstruction, the same may be applied to other surgical procedures where locating a second tunnel relative to a first tunnel in bone is desired.

At the outset, an exemplary procedure for preparing a tibial tunnel and a femoral tunnel will be described. For a knee reconstruction involving an un-repairable or torn ACL, the procedure may begin with a general anesthesia being administered to the patient. The patient may be positioned supine on an operating table. A well-padded tourniquet may be placed proximal on the thigh of the affected leg. An arthroscopic leg holder may be placed around the tourniquet. The table may be inclined (e.g. 15 degrees of trendelenburg) and adjusted in height (e.g. waist level) according to the desires of the surgeon. The other leg may be secured to the foot of the table. A Mayo stand may be placed over the leg holder and positioned to permit access to the lateral thigh.

The surgical site may be prepped and draped with a sterile seal. Standard arthroscopic draping may be performed covering the Mayo stand. A light cord, camera, motorized instruments, inflow, outflow and suction tubing may be wrapped and secured to the drape on the Mayo stand. An irrigation stand may be set up and positioned. The joint of the affected leg may be examined physically to confirm a rupture of the ACL and to determine the amount and degree of movement.

The graft harvesting step in the procedure depends on the type of ACL substitute that is to be utilized. In one example, the gracilis and semi-tendinosus tendons are harvested from the patient and used as the ACL substitute. In general these may provide grafts which are stronger in the joint than the original ACL and have less postoperative morbidity. In other examples, patellar tendons, autogenous tendons, frozen and lyophilized tendon allografts, or some of the various known synthetic materials may be used as ACL substitute.

After the grafts are harvested, they may be prepared and sized. In one example, a surgical assistant may prepare and size the grafts while the surgeon continues with the rest of the ACL replacement procedure. Sutures may be attached to the ends of the grafts to aid in grasping, manipulating and securing the grafts in place. Incremental sizing tubes may be used to size the grafts and select the appropriate drills for forming the tunnels. For purposes of discussion, the grafts will hereinafter be referred to as an anterior medial (AM) bundle and a posterior lateral (PL) bundle.

The prepared knee may now be examined by arthroscopic procedures. Standard anterolateral and anteromedial portals may be made for the diagnostic arthroscopy. Proper portal placement is important. In one example, the lateral portal may be made at a location one-third the width of the patella ligament medial to the lateral margin and positioned vertically just inferior to the inferior patella tip. The medial portal may be made vertically, just inferior to the inferior patella tip and adjacent to the medial border of the patella ligament. The two portals may be located at the same level.

In one example, wallplasty may be performed to remove a portion of the lateral condylar wall. A tool such as an up-angled, curved and uterine curette may be used to remove the origin (and stump) of the ACL from the intercondylar roof and the wall of the lateral femoral condyle. The retained synovial and cruciate remnants may be cleaned and vacuumed with a full-radius resector.

Next, a tibial tunnel 10 (FIG. 1) is prepared. In one example, a Howell™ 65° Tibial Guide (Howell Guide, not shown) may be used to prepare the tibial tunnel 10. The Howell Guide and a method of using may be found in U.S. Pat. No. 6,254,605, which is incorporated by reference.

Figure 2:
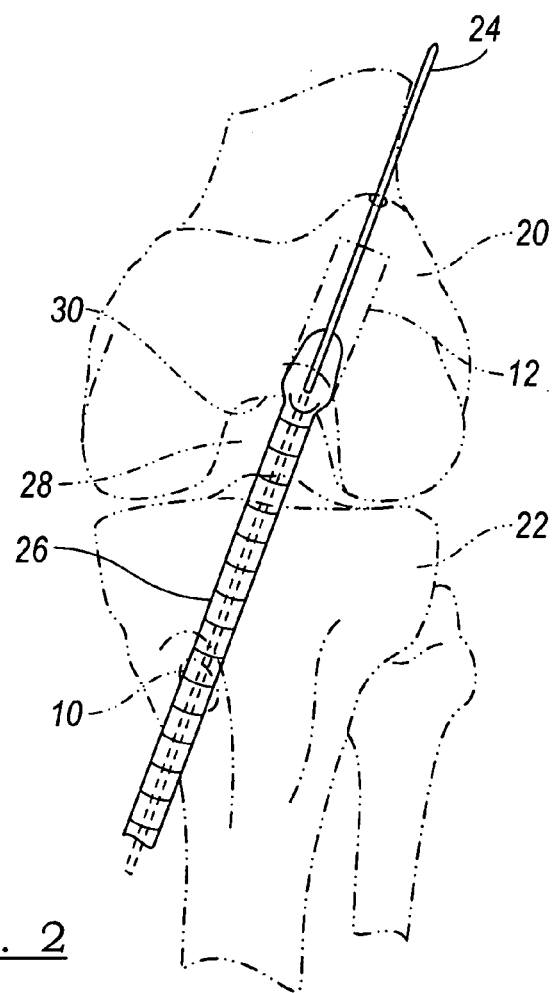
FIG. 2 is an anterior view of the knee illustrated in FIG. 1 shown with a calibrated acorn reamer used to determine the length of the femoral tunnel.

With reference now to FIGS. 1 and 2, an exemplary method of preparing the femoral AM tunnel 12 will be described. Once the tibial tunnel 10 has been prepared, a femoral aimer 16 may be inserted through the tibial tunnel 10. In one example, a 12 mm femoral aimer 16 may be used. The femur 20 may then be flexed to 90° relative to the tibia 22. The femoral aimer 16 may then be laterally angulated and externally rotated away from the PCL (not shown). A graft passing pin 24 may then be drilled through the lateral thigh. The length of the femoral AM tunnel 12 may be equal to the length of the AM graft minus the length of the tibial tunnel 10 and notch (FIG. 2). A calibrated acorn reamer 26 may be used to measure the length of the tibial tunnel and notch 28. The acorn reamer 26 may be inserted over the graft passing pin 24 until it touches the intercondylar roof 30. The length of the acorn reamer 26 at the point the reamer 26 exits the tibial tunnel 10 is recorded. The acorn reamer 26 may then be used to drill the femoral AM tunnel 12 to the calculated length.

One exemplary method of securing the replacement grafts to the respective AM and PL tunnels includes using interference screws such as a TunneLoc® Interference Screw manufactured by the assignee of the present disclosure. Although the following discussion will be directed toward utilizing interference screws, other methods may be used to secure the respective AM and PL bundles within the AM and PL tunnels. When preparing the AM and PL tunnels for interference screws, a tunnel notcher (not shown) may be used to notch the anterior rim of the AM and PL tunnels to facilitate improved contact with the interference screw.

With reference now to FIGS. 3A, 3B, 4 and 7, an exemplary tool 34 for preparing a PL tunnel 36 (FIG. 7) relative to the AM tunnel 12 will be described. It is appreciated however, that although the following discussion is directed toward locating the PL tunnel 36 relative to the AM tunnel 12, the tool 34 may be used to locate any tunnel relative to an already prepared tunnel. For example, the tool 34 may be used to locate the AM tunnel 12 relative to an already prepared PL tunnel 36. In another example, the tool 34 may be used to locate one bone tunnel relative another bone tunnel for receipt of a dual bundle (anterolateral bundle and posteromedial bundle) posterior cruciate ligament (PCL) replacement.

The tool 34 generally defines a first and second longitudinal member 40 and 42 defining a first and second axis 44 and 46, respectively. The first longitudinal member 40, hereinafter referred to as an aimer, includes a foot or locating member 50 extending outwardly therefrom. The locating member 50 defines a locating axis 52. In one example, the locating axis 52 may define an angle α relative to the first axis 44 of the aimer 40. The second longitudinal member 42, hereinafter referred to as a cutting guide, is adapted to slidably translate within a cannulation defined in the aimer 40. The cutting guide 42 may selectively retain a cutting member or drill 56 at a distal end 58. The drill 56 defines a cutting axis 60. In another example, the drill 56 may be integrally formed with the cutting guide 42.

Figure 3A:
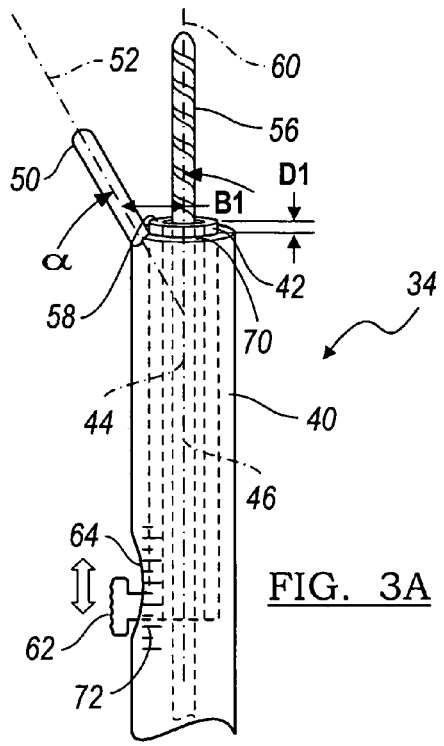
FIG. 3A is a side perspective view of an exemplary tool used to prepare a second bone tunnel relative to an already prepared first bone tunnel shown in a first position.
Figure 3B:
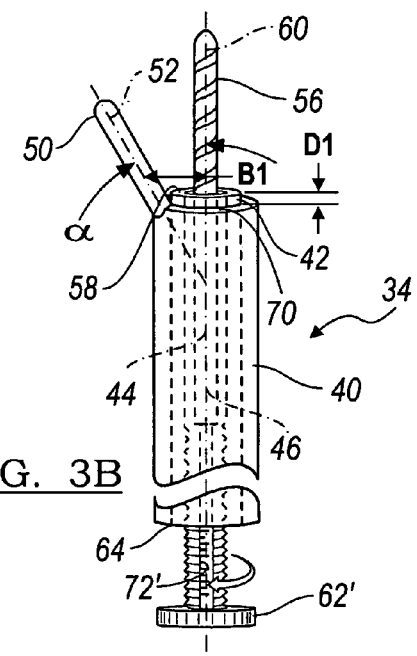
FIG. 3B is a side perspective view of an exemplary tool according to additional features used to prepare a second bone tunnel relative to an already prepared first bone tunnel shown in a first position.

The cutting guide 42 is adapted to be linearly translated within the aimer 40. In the exemplary tool 34, a handle 62 may be provided on a proximal end 64 of the cutting guide 42 and adapted to extend through a slot 64 defined on the aimer 40. As a result, a surgeon may manipulate the handle 62 along the slot 64 to alter a distance D1 measured between the distal end 58 of the cutting guide 42 and a distal end 70 of the aimer 40. It is appreciated that the handle configuration is merely exemplary and many other mechanical arrangements may be provided for allowing a surgeon to translate the cutting guide 42 within the aimer 40. For example, as shown in FIG. 3B, a threaded rod 62' may be provided. The threaded rod 62' may be rotated and threadably advanced relative to the aimer 40.

Figure 4:
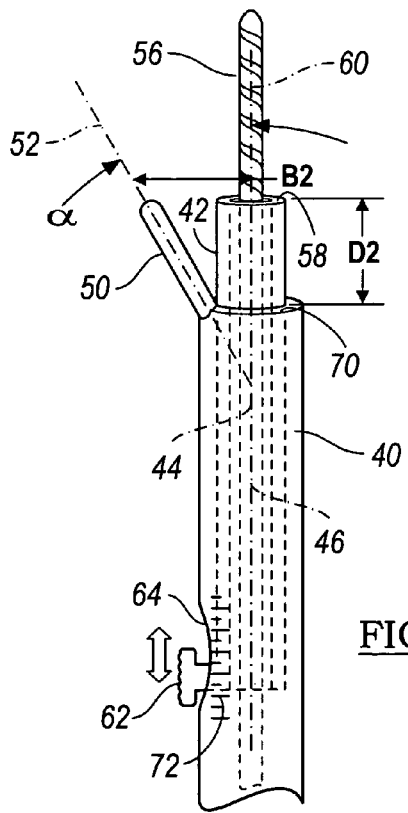
FIG. 4 is a side perspective view of the tool of FIG. 3 shown in a second position.

Translation of the cutting guide 42 relative to the aimer 40 allows the surgeon to select a desired distance or bridge between the drill 56 and the foot 50. As illustrated in FIG. 3, a first distance B1 is defined transverse to a centerline (cutting axis 60) of the drill 56 to a centerline (locating axis 52) of the foot 50. Translation of the cutting guide 42 within the aimer 40 alters the distance D1. As illustrated in FIG. 4, a second distance B2 is defined transverse to the centerline of the drill 56 to the centerline of the foot 50. As a result, the surgeon may drill the PL tunnel at a desired location relative to the AM tunnel for a given patient. In one example indicia 72 (72', FIG. 3B) may be provided on the aimer 40 or the handle 62 (62', FIG. 3B) that correspond to the bridge measurement B1, B2. It is appreciated that while the bridge between tunnels may be modified for a given patient, the angle α remains constant. It is contemplated that a series of aimers may be provided each having a distinct angle α. For example, aimers may be provided for locating a second tunnel (in this exemplary case, the PL tunnel) at angles such as 5, 10, 15, 20, 25 degrees or others relative to the first tunnel. In another example, the foot 50 may be adjustable such that the surgeon may set a desired angle of the foot 50 relative to the aimer 40. In yet another example, the length of the foot 50 may be adjustable such that the surgeon may extend or retract the foot 50 for a given application.

Figure 7:
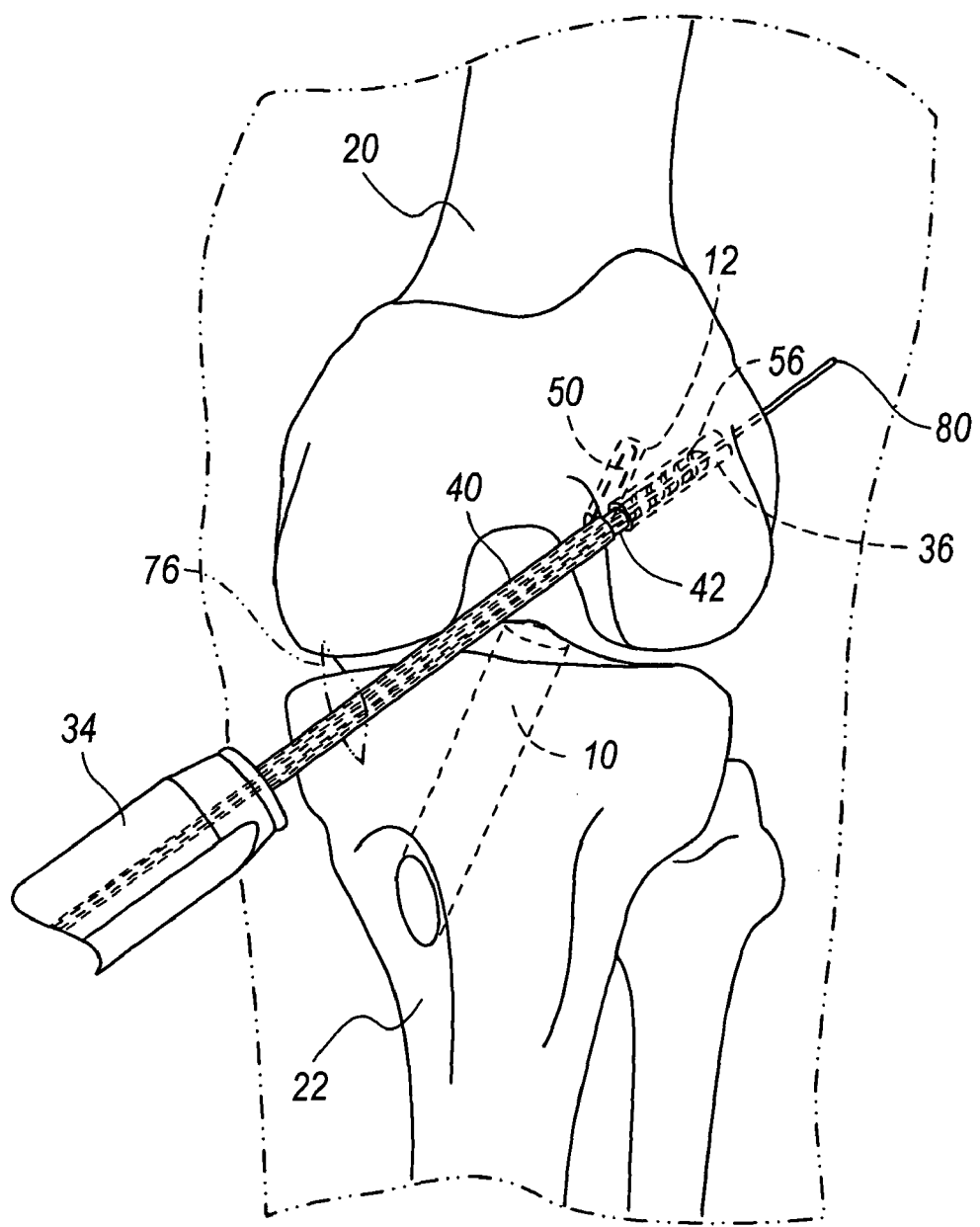
FIG. 7 is an anterior view of the knee shown with the tool inserted through an anterior medial (AM) portal during use according to an exemplary method.

With specific reference to FIG. 7, an exemplary method of using the tool 34 will be described. At the outset, the tool 34 may be inserted through an AM portal 76 until the foot locates into the AM tunnel 12. Next, the surgeon may translate the cutting guide 42 relative to the aimer 40 until a desired bridge is defined. In one example, it may be necessary to hold the foot 50 against the tunnel wall of the AM tunnel 12 to assure the foot 50 is parallel to the AM tunnel 12. In another example, an outer diameter of the foot 50 may be slightly less than an inner diameter of the AM tunnel 12 to encourage a tolerance fit and parallel alignment. During translation of the cutting guide 42, it may be necessary to partially retract or further insert the foot 50 relative to the AM tunnel 12. Once the desired bridge is verified, a guide wire 80 may then be advanced through the femur 20. The drill 56 is then used to ream the PL tunnel 36. While not specifically shown, it is appreciated that a conventional driver may be coupled to the drill 56 to provide rotational movement of the drill 56.

Figure 8:
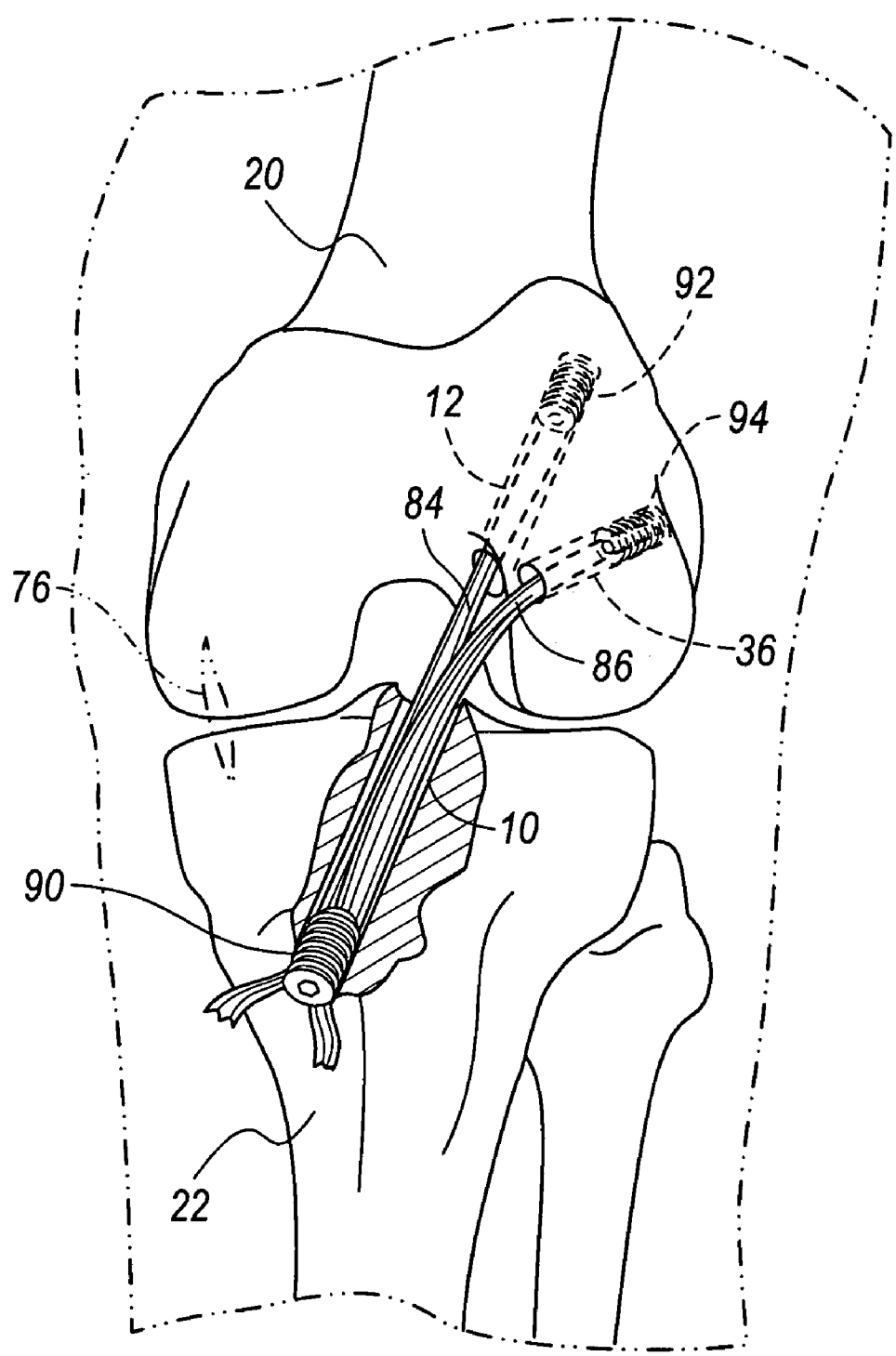
FIG. 8 is an anterior view of the knee shown with AM and posterior lateral (PL) bundles secured by anchors in respective AM and PL tunnels according to an exemplary method.

Turning now to FIG. 8, an exemplary method for securing an AM bundle 84 and a PL bundle 86 to the AM tunnel 12 and PL tunnel 36, respectively will be described. Interference screws such as TunneLoc® Interference Screws 90, 92 and 94 may be driven by conventional methods into tunnels 10, 12 and 36 respectively to securely locate the AM bundle 84 and PL bundle 86.

Figure 9A:
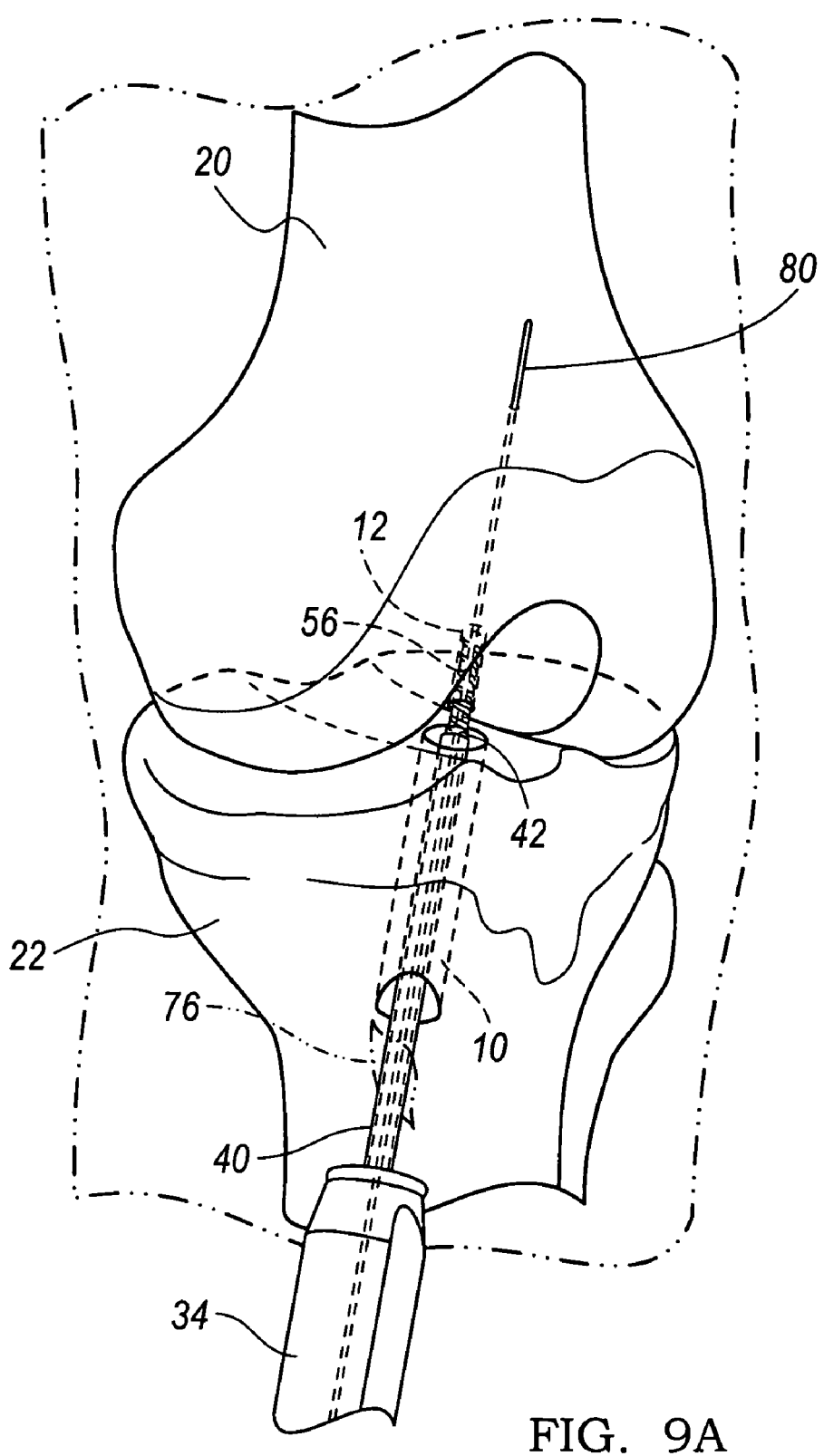
FIG. 9A is an anterior view of the knee shown with the tool inserted through a tibial tunnel and locating the AM portal according to an exemplary method.
Figure 9B:
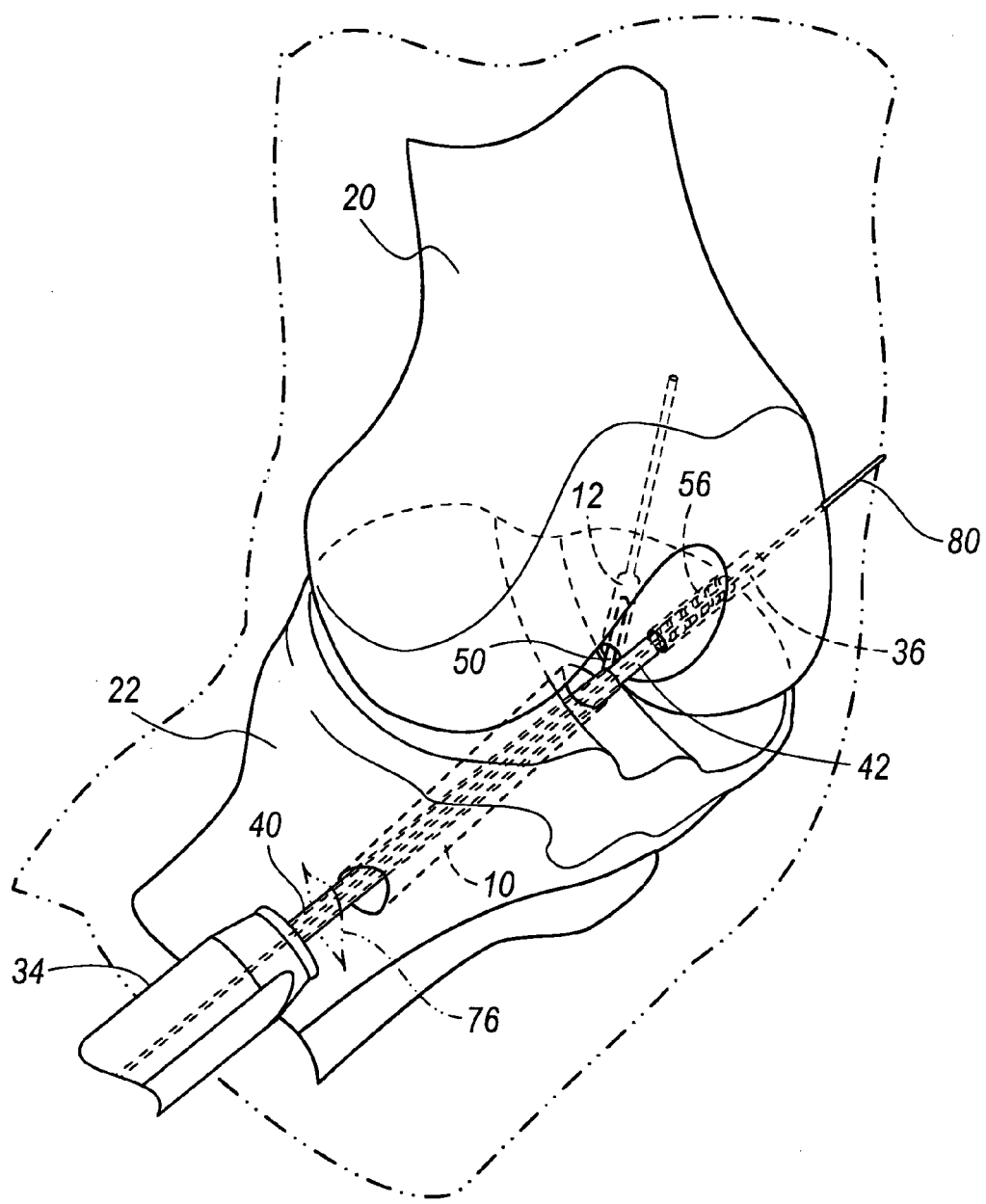
FIG. 9B is an anterior lateral view of the knee with the tool inserted through a tibial tunnel during use according to another exemplary method.

Referring now to FIGS. 9A and 9B, another exemplary method of using the tool 34 will be described. In this method, the tool may be inserted through the tibial tunnel 10 until the foot 50 locates within the AM tunnel 12. As shown in FIG. 9B, the aimer 40 may be cocked in the tibial tunnel 10 to assure the foot 50 located properly with the AM tunnel 12.

Figure 10:
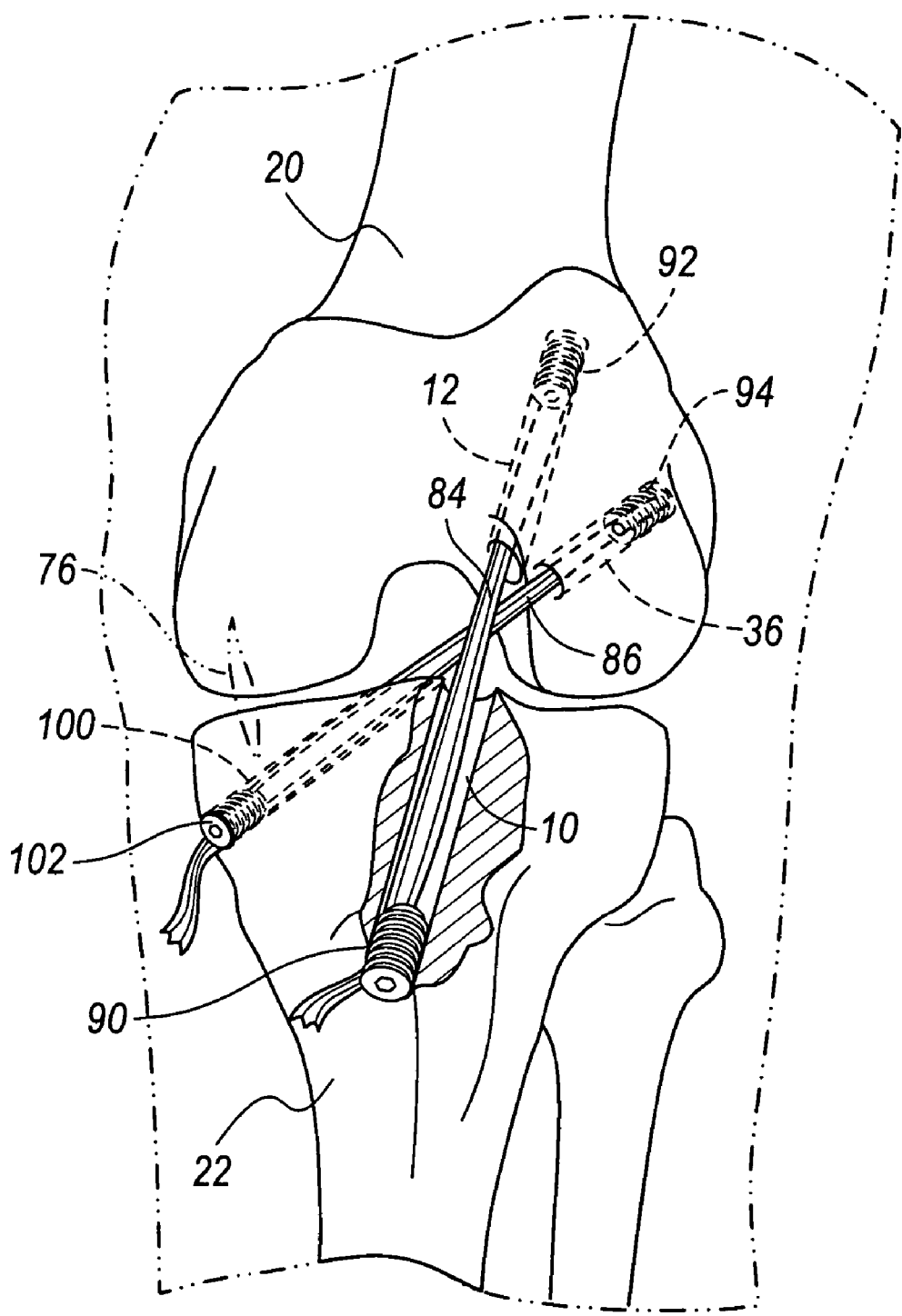
FIG. 10 is an anterior view of the knee shown with AM and PL bundles secured by anchors in respective AM and PL tunnels according to another exemplary method.

As illustrated in FIG. 10, according to another exemplary method, a pair of distinct tibial tunnels 10, 100 may be prepared in the tibia 22. As a result, the AM bundle 84 and the PL bundle 86 may both be located in distinct tibial tunnels. A fourth bone screw 102 may be used to secure the tibial end of the PL bundle 86. The tibial tunnel 100 may be prepared by any suitable method, such as by utilizing a k-wire and cannulated drill.

Figure 5:
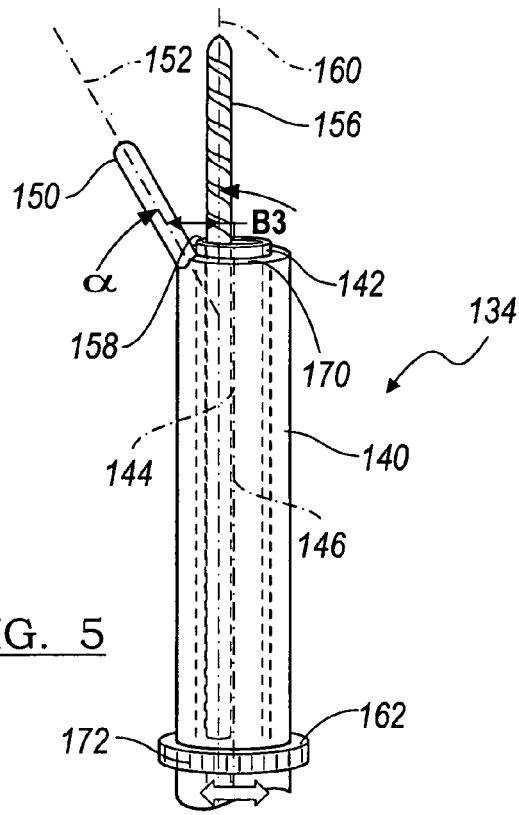
FIG. 5 is a side perspective view of an exemplary tool according to additional features used to prepare a second bone tunnel relative to an already prepared first bone tunnel shown in a first position.
Figure 6:
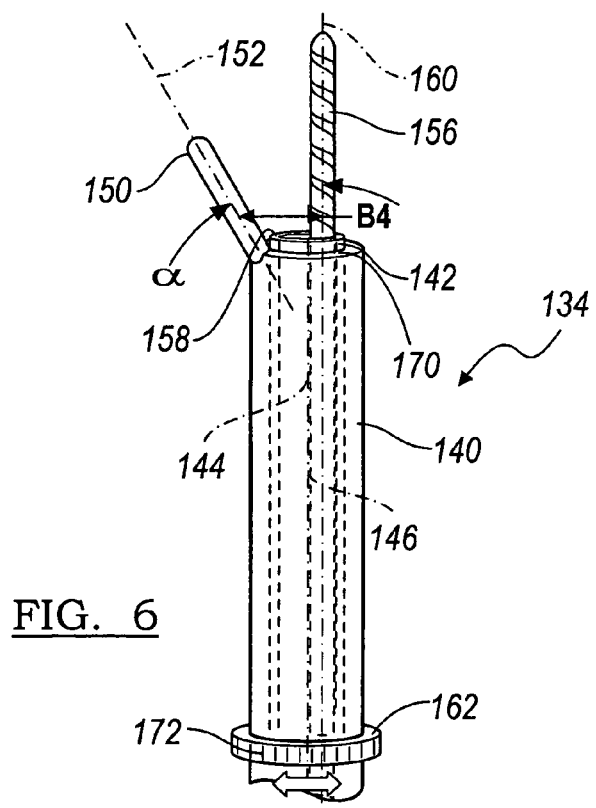
FIG. 6 is a side perspective view of the tool of FIG. 5 shown in a second position.

Referring now to FIGS. 5 and 6, a tool 134 according to additional features will be described. The tool 134 includes similar features as the tool 34. As a result, like reference numerals increased by 100 are used for the tool 134. The drill 156 is located in an offset relationship with respect to the cutting guide 42. In this way, the cutting axis 160 is offset from the second axis 146. The tool 134 includes a rotating dial 162 adapted to rotate the cutting guide 142 within the aimer 140. In the exemplary views shown in FIGS. 5 and 6, the dial is positioned at a location corresponding to the smallest available bridge B3 (FIG. 5) and the largest available bridge B4 (FIG. 6). It is appreciated that many measurements intermediate B3 and B4 are available. Indicia 172 may be provided on the dial 162 corresponding to the bridge measurement. Again, the angle α remains constant throughout rotation of the dial 162. As with the tool 34, a series of aimers may be provided for defining various angles. The exemplary cutting guide 142 defines a circular cross section. It is appreciated that a series of bridge measurements may be attained throughout 360 degrees of rotation of the cutting guide 142. In another arrangement, a linear slot may be defined at the distal end 158 of the cutting guide 142 in a direction perpendicular to the cutting axis 160. A rotating dial, such as the dial 162 or a handle, such as the handle 162 may be utilized to translate the drill 152 along the linear slot. Other configurations may be used.

Those skilled in the art can now appreciate from the foregoing description that the broad teachings of the present invention can be implemented in a variety of forms. For example, while the preceding discussion explains first, forming a passage in the tissue and subsequently passing the apparatus through the passage, the same may be accomplished simultaneously. In one example, a hollow piercing member may carry the apparatus and concurrently form the passage while depositing the apparatus through the passage. Therefore, while this invention has been described in connection with particular examples thereof, the true scope of the invention should not be so limited since other modifications will become apparent to the skilled practitioner upon a study of the drawings, the specification and the following claims.

What is claimed is:

1. A method for drilling a bone for receipt of a first and second bundle, the method comprising:

drilling a first tunnel in the bone;

subsequently to the drilling, positioning a locating member extending from a tool along a first axis into the drilled first tunnel;

slidably translating a cutting guide associated with a cutting member in a direction along a second axis, while selectively retaining the cutting member within a cannulated sleeve, the second axis of the cutting member being in a defined orientation relative to the first axis;

moving the cutting member that extends through a bore in the tool relative to the locating member while the locating member remains positioned in the drilled first tunnel to select a desired lateral offset between the locating member and the cutting member; and forming a second tunnel in the bone with the cutting member.

2. The method of claim 1 wherein a first perpendicular distance is defined from a point on the cutting member to the locating member, wherein translation of the cutting guide along its axis defines a second perpendicular distance from the point on the cutting member to the locating member and wherein the first and second distances are distinct.

3. A method for drilling a bone for receipt of a first and second bundle, the method comprising:

drilling a first tunnel in the bone;

subsequently to the drilling, positioning a locating member extending from a tool alone a first axis into the drilled first tunnel;

moving the cutting member that extends through a bore in the tool relative to the locating member in a direction lateral to an axis of the cutting member while the locating member remains positioned in the drilled first tunnel to select a desired lateral offset between the locating member and the cutting member; and forming a second tunnel in the bone with the cutting member, the cutting member having a second axis in a defined orientation relative to the first axis.

4. The method of claim 3 wherein moving the cutting member includes:

rotating a cutting guide associated with said cutting member while selectively retaining the cutting member within a cannulated sleeve, wherein the cutting guide defines a guide axis offset from the second axis.

5. The method of claim 4 wherein a first perpendicular distance is defined from a point on the cutting member to the locating member, wherein moving the cutting member in a direction lateral to its axis defines a second perpendicular distance from the point on the cutting member to the locating member and wherein the first and second distances are distinct.

6. The method of claim 3, further comprising:

passing the first bundle through one of the first and second tunnels;

passing the second bundle through the other tunnel; and securing the first bundle and the second bundle to the bone.

7. The method of claim 6 wherein the bone comprises a femur.

8. The method of claim 7 wherein the first tunnel comprises one of an anterior medial tunnel and a posterior lateral tunnel and wherein the second tunnel comprises the other of the anterior medial tunnel and a posterior lateral tunnel.

9. The method of claim 7 wherein positioning a locating member extending from a tool into the first tunnel further comprises:

inserting the tool through an anterior medial portal.

10. The method of claim 9, further comprising drilling a third tunnel in a second bone and wherein positioning the locating member extending from a tool into the first tunnel comprises locating the tool through the third tunnel.

11. The method of claim 10 wherein the second bone comprises a tibia and wherein the third tunnel comprises a tibial tunnel.

12. A method for drilling a bone for receipt of a first and second bundle, the method comprising:

drilling a first tunnel in a femur at a first entry point;

positioning a locating member extending from a tool along a first axis through the first entry point and into the first tunnel;

slidably translating a cutting guide that extends through a bore in the tool relative to the locating member in a direction alone an axis of the cutting guide while the locating member remains positioned in the first tunnel while selectively retaining a cutting member associated with the cutting guide within a cannulated sleeve to define at least two lateral offsets between the locating member and the cutting guide;

locating the cutting guide at a desired offset from the at least two lateral offsets; and forming a second tunnel at a second entry point in the femur with the cutting member, the cutting member having a second axis in a defined orientation relative to the first axis.

13. The method of claim 12 wherein drilling the first tunnel and positioning the locating member comprise advancing a drill and the locating member into the femur along a common direction.

14. A method for drilling a bone for receipt of a first and second bundle, the method comprising:

drilling a first tunnel in a femur at a first entry point;

positioning a locating member extending from a tool alone a first axis through the first entry point and into the first tunnel;

threadably translating a cutting guide that extends through a bore in the tool relative to the locating member in a direction alone an axis of the cutting guide while the locating member remains positioned in the first tunnel while selectively retaining a cutting member associated with the cutting guide within a cannulated sleeve to define at least two lateral offsets between the locating member and the cutting guide;

locating the cutting guide at a desired offset from the at least two lateral offsets; and forming a second tunnel at a second entry point in the femur with the cutting member, the cutting member having a second axis in a defined orientation relative to the first axis.

15. A method for drilling a bone for receipt of a first and a second bundle, the method comprising:

drilling a first tunnel into a femur by advancing a drill along a first direction;

removing the drill from the first tunnel;

inserting a tool through an anterior medial portal;

positioning a locating member extending from the tool into the first tunnel alone the first direction;

slidably translating a cutting guide that extends through a bore in the tool relative to the locating member in a direction along an axis of the cutting guide while selectively retaining a cutting member within a cannulated sleeve to select a desired lateral offset between the locating member and the cutting guide; and drilling a second tunnel into the femur with the cutting member extending from said cutting guide.

16. A method for drilling a bone for receipt of a first and a second bundle, the method comprising:

drilling a first tunnel into a femur by advancing a drill alone a first direction;

removing the drill from the first tunnel;

inserting a tool through an anterior medial portal;

positioning a locating member extending from the tool into the first tunnel along the first direction;

rotating a cutting guide while selectively retaining a cutting member within a cannulated sleeve, a cutting guide that extends through a bore in the tool relative to the locating member to select a desired lateral offset between the locating member and the cutting guide; and drilling a second tunnel into the femur with the cutting member extending from said cutting guide, the cutting member having a second axis, wherein the cutting guide defines a guide axis offset from the second axis.

17. The method of claim 16 wherein the first direction is the superior lateral direction.

* * * * *

UNITED STATES PATENT AND TRADEMARK OFFICE
CERTIFICATE OF CORRECTION

| | | |
|---|---|---|
| PATENT NO. | : 7,736,364 B2 | Page 1 of 1 |
| APPLICATION NO. | : 11/346534 | |
| DATED | : June 15, 2010 | |
| INVENTOR(S) | : Kevin T. Stone | |

It is certified that error appears in the above-identified patent and that said Letters Patent is hereby corrected as shown below:

In the Specification:

Column 1, line 17, delete "or" and replace with "of".

Column 6, line 6, insert --is-- after "foot 50".

Column 6, line 38, delete "handle 162" and replace with "handle 62".

In the Claims:

Column 7, line 19, Claim 3, delete "alone" and replace with "along".

Column 8, line 9, Claim 12, delete "alone" and replace with "along".

Column 8, line 28, Claim 14, delete "alone" and replace with "along".

Column 8, line 33, Claim 14, delete "alone" and replace with "along".

Column 8, line 53, Claim 15, delete "alone" and replace with "along".

Column 8, line 64, Claim 16, delete "alone" and replace with "along".

Signed and Sealed this

Twenty-fourth Day of August, 2010

David J. Kappos
*Director of the United States Patent and Trademark Office*